US011517385B2

(12) United States Patent
Stefan (10) Patent No.: US 11,517,385 B2
(45) Date of Patent: Dec. 6, 2022

(54) MEDICAL INSTRUMENT

(71) Applicant: KARL STORZ SE & Co. KG, Tuttlingen (DE)

(72) Inventor: Jochen Stefan, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 0 days.

(21) Appl. No.: 17/584,952

(22) Filed: Jan. 26, 2022

(65) Prior Publication Data

US 2022/0233266 A1 Jul. 28, 2022

(30) Foreign Application Priority Data

Jan. 27, 2021 (DE) .................... 10 2021 101 766.1

(51) Int. Cl.
*A61B 34/00* (2016.01)
*A61B 34/30* (2016.01)

(52) U.S. Cl.
CPC ........ *A61B 34/71* (2016.02); *A61B 2034/301* (2016.02); *A61B 2034/715* (2016.02)

(58) Field of Classification Search
CPC .............. A61B 34/71; A61B 2034/301; A61B 2034/715; A61B 17/29; A61B 2017/003;
(Continued)

(56) References Cited

U.S. PATENT DOCUMENTS 5,454,827 A 10/1995 Aust et al.
2007/0129605 A1* 6/2007 Schaaf ............... A61B 1/00082
600/116
(Continued)

FOREIGN PATENT DOCUMENTS

KR 10-2010-0137652 A 12/2010
WO WO 2013/180041 A1 12/2013
(Continued)

OTHER PUBLICATIONS

German Office Action (Including Translation) for German Application No. 10 2021 101 766.1, dated Oct. 29, 2021.

*Primary Examiner* — Gary Jackson
*Assistant Examiner* — Sebastian X Lukjan
(74) *Attorney, Agent, or Firm* — Jason H. Vick; Sheridan Ross, PC (57) ABSTRACT

The disclosure relates to an actuation unit (16) for a medical instrument (10) and to a medical instrument (10) with a shaft (12) which extends between a proximal end (20) and a distal end (22), wherein the instrument (10) is designed at the distal end (22) to receive an end effector (14), an actuation unit (16, 216) which is assigned to the proximal end of the shaft (12), and which has a plurality of drives (50, 52, 54, 56), and with at least two control trains (100, 102, 104, 106, 108, 110, 112, 114) which extend through the shaft (12), wherein the at least two control trains (100, 102, 104, 106, 108, 110, 112, 114) can be used for controlling at least one degree of freedom of the instrument, in particular for deflecting the end effector (14), wherein the at least two control trains (100, 102, 104, 106, 108, 110, 112, 114) comprise a first control train (100, 104, 108, 112) and a second control train (102, 106, 110, 114), and wherein the first control train (100, 104, 108, 112) is coupled to a first carrier (70, 74, 78, 82) and the second control train (102, 106, 110, 114) is coupled to a second carrier (72, 76, 80, 84), on which a drive (50, 52, 54, 56) acts for generating a pushing movement or pulling movement of the carrier (70, 72, 74, 76, 78, 80, 82, 84).

15 Claims, 5 Drawing Sheets

(58) Field of Classification Search
CPC .......... A61B 2017/00314; A61B 2017/00398; A61B 2017/2908; A61B 34/30; A61B 2034/305; A61B 1/0052; A61B 1/005; A61B 1/0055
See application file for complete search history.

(56) References Cited

U.S. PATENT DOCUMENTS

| | | | | |
|---|---|---|---|---|
| 2007/0282371 | A1* | 12/2007 | Lee | A61B 17/29 606/205 |
| 2010/0030018 | A1* | 2/2010 | Fortier | A61B 18/1445 600/104 |
| 2018/0049817 | A1 | 2/2018 | Swayze et al. | |
| 2020/0352666 | A1* | 11/2020 | Danitz | A61B 34/77 |
| 2021/0401487 | A1* | 12/2021 | Apostolopoulos | A61B 34/37 |

FOREIGN PATENT DOCUMENTS

| | | | | |
|---|---|---|---|---|
| WO | WO-2018189722 A1 * | 10/2018 | ............. | A61B 17/29 |
| WO | WO-2019191413 A1 * | 10/2019 | ............. | A61B 34/35 |

* cited by examiner

MEDICAL INSTRUMENT

CROSS-REFERENCE TO RELATED APPLICATIONS

This application claims the benefit under 35 U.S.C. 119(a) to German Patent Application No. 10 2021 101 766.1, filed 27 Jan. 2021, the disclosure of which is incorporated herein by reference in its entirety

BACKGROUND

The present disclosure relates to a medical instrument with a shaft which extends between a proximal end and a distal end, wherein the instrument is designed at the distal end to receive an end effector, an actuation unit which is assigned to the proximal end of the shaft, and with at least two control trains which extend through the shaft, wherein the at least two control trains can be used for controlling at least one degree of freedom of the instrument, in particular for deflecting the end effector.

U.S. Pat. No. 5,454,827 A has disclosed a surgical instrument having a rigid shaft with a distal end and a proximal end, said rigid shaft extending between a handle and a jaw head, a deflectable portion being provided at the distal end of the rigid shaft and permitting a deflection of the jaw head relative to the rigid shaft in any desired directions, the deflectable portion having a plurality of pivot joints which are arranged in series and are pivotable relative to one another.

To control the deflection movement, U.S. Pat. No. 5,454,827 A proposes the use of four actuation wires which extend through the shaft and the deflectable portion and which can be manually operated via a control lever. The four actuation wires are coupled to a distal member of the deflectable portion, and to a control plate connected to the control lever, in such a way that, upon a deflection of the control lever, the actuation wires are in part pulled in the proximal direction or pushed in the distal direction. In this way, the jaw head can be deflected up or down or to the right or left, for example.

Medical instruments of a wide variety of types are known. For example, there are medical instruments with an end effector in the form of a jaw head which has two jaw parts that are movable relative to each other in order to open or close the jaw head. Instruments of this kind are designed, for example, as clamps, scissors, staplers, forceps, tweezers or similar. Relevant medical instruments are also known which are designed for electrosurgical treatment and have one or more electrodes in the region of the jaw head.

It will be appreciated that the end effector in some examples is not necessarily designed as a jaw head. For example, the end effector can comprise optical elements and/or an image recorder. For example, the end effector is designed to output electromagnetic radiation, for example in the context of photodynamic therapy. For example, the end effector is designed for removing samples and/or for delivering a therapeutic agent or other substances. The end effector can also be designed, for example, to provide an irrigation function and/or suction function. Mixed forms and combinations are conceivable.

Particularly in instruments with a rigid shaft, additional degrees of freedom are often desired, for example in order to permit a deflection of the end effector relative to the shaft. In this way, for example, the end effector (as viewed by the operator) can be deflected up or down or to the right or left. U.S. Pat. No. 5,454,827 A describes an embodiment in which a deflection of a jaw head in several directions is permitted using just one control lever.

The surgical instrument described in U.S. Pat. No. 5,454,827 A is guided by hand, and the deflectable portion is likewise controlled manually. The operator can steer the control lever in different directions, similarly to a joystick, and the jaw head is deflected in response to this.

Medical instruments with motorized and in some cases even robotic control have been known for some time. Some or all degrees of freedom (movements, functions, etc.) of the instrument can be actuated by motor and, if appropriate, controlled. This can afford advantages during operation of the instruments. Moreover, further developments such as remote medicine (remote surgery), surgical treatments with surgical robots and similar require almost complete motorized/robotic control of all or almost all the functions of the instrument.

The concept disclosed in U.S. Pat. No. 5,454,827 A is suitable for manual actuation, assuming a suitable level of experience of the operator. However, a one-to-one conversion would lead to high outlay, because the control movement at the control lever includes various degrees of freedom of movement.

In medical instruments, particularly in surgical instruments or in instruments for minimally invasive surgery, strict limitations on the installation space often have to be taken into consideration. This often applies to a shaft diameter. For example, the diameter of a shaft of a medical instrument can be at most 15 mm, at most 12 mm, at most 10 mm, at most 8 mm, or even at most 6 mm. This is not to be understood as restrictive. Similarly, various functions and degrees of freedom are often desired for the end effector. Corresponding movements have to be regularly transmitted from the proximal end of the instrument to the distal end. Drives or other actuators cannot generally be realized directly at the end effector.

Against this background, the object of the present disclosure is to provide a medical instrument which has a plurality of degrees of freedom, in particular degrees of freedom of movement, for an end effector, wherein at least some of the degrees of freedom can be controlled by motor. This applies for example to a deflection movement of the end effector. The instrument preferably permits a small shaft diameter. The instrument preferably permits a deflection of the end effector in different directions. The deflection of the end effector can preferably be variably controlled. The deflection movement preferably entails no play or minimal play. In particular, the medical instrument should be suitable for use in remote medical (remote surgical) treatment and/or robotic or robot-assisted surgery, at least in exemplary embodiments.

Furthermore, the object of the present disclosure is to provide an actuation unit suitable for such an instrument.

According to a first aspect, the present disclosure relates to a medical instrument with a shaft which extends between a proximal end and a distal end, wherein the instrument is designed at the distal end to receive an end effector, an actuation unit which is assigned to the proximal end of the shaft, and which has a plurality of drives, and with at least two control trains which extend through the shaft, wherein the at least two control trains can be used for controlling at least one degree of freedom of the instrument, in particular for deflecting the end effector, wherein the at least two control trains comprise a first control train and a second control train, and wherein the first control train is coupled to a first carrier and the second control train is coupled to a second carrier, on which a drive acts for generating a pushing movement or pulling movement of the carrier.

The object is achieved in this way.

According to the invention, an actuation unit is in fact made available which if necessary is able to control quite complex movements (degrees of freedom of the instrument) but which, for this task, uses only simple elements that are suitably coupled to one another. In particular, simple movements (pulling movements or pushing movements) are used to control the desired degrees of freedom of movement of the instrument. Pulling movements or pushing movements are generally translational movements which, for example, can be generated precisely and reproducibly with threaded spindles. Complex movements can accordingly be divided into a plurality of simple partial movements, for which purpose established drives, in particular electromotive drives, are available.

In the context of the present disclosure, a distal end or element is directed toward a patient and directed away from an operator and/or a base of the instrument. In the context of the present disclosure, a proximal end or element is directed toward an operator or a base of the instrument and directed away from a patient. In other words, a distal end or element of a unit is generally arranged closer to the patient than a proximal element of the same unit. The term "distal" can therefore also be understood as "toward the patient". The term "proximal" can therefore also be understood as "away from the patient".

In the context of the present disclosure, a pulling movement of a carrier is a movement of the carrier in the proximal direction, for example away from the distal end. In the context of the present disclosure, a pushing movement of a carrier is a movement of the carrier in the distal direction, for example away from the proximal end.

For example, the deflection of the instrument is a deflection of the end effector in relation to the shaft and/or in relation to the proximal end of the instrument. A deflection of the end effector comprises, for example, a transition from an extended orientation (for example concentric to the longitudinal axis of the shaft) to an orientation at an angle to the longitudinal axis.

In an exemplary embodiment, an end effector is arranged at the distal end of the shaft of the instrument. The end effector is, for example, a jaw head with two jaw parts, of which at least one jaw part is movable relative to the other jaw part. Such a jaw head is designed, for example, in the form of forceps, tweezers, scissors, a coagulation instrument or similar. In exemplary embodiments, the end effector comprises a light source or radiation source. In exemplary embodiments, the end effector comprises structural parts of an optical assembly. In an exemplary embodiment, the end effector comprises an image recorder.

An end effector can also be described as a distal endpiece of the instrument arranged at the distal end of the shaft. It will be appreciated that further structural parts can be formed between the shaft and the end effector, for example a deflectable portion. In some embodiments, the deflectable portion is a constituent part of the shaft.

When a pushing movement or pulling movement of the carrier is generated, the control train coupled thereto can be subjected to tension (pulled in the proximal direction) or to thrust (generally: compensating movement in the distal direction). This can be used to generate a movement at the distal end of the instrument. Moreover, the one or more control trains, in particular the two control trains of a pair, can be slightly pretensioned in order to minimize or even eliminate a movement play (for example reversal play) during the control of the degree of freedom of the instrument. This permits highly precise movements with a high degree of reproducibility.

In exemplary embodiments, the actuation unit is designed as a motorized actuation unit with motorized drives. In this way, the instrument can be used for remote medical applications, remote surgical applications, robot-assisted applications and the like.

In the context of the present disclosure, ordinal numbers (first, second, third element, etc.) are used primarily to distinguish between different elements. They do not entail a weighting or ranking. In other words, embodiments are conceivable in which only a second or third element of a list is provided, not the first element.

In exemplary embodiments, the medical instrument is designed for insertion into a body of a patient. This can take place via natural or artificial openings in the body. It will be appreciated that the medical instrument can also be designed for treatment of the body from outside of the body.

In particular, the medical instrument is a surgical instrument. For example, the medical instrument is an instrument for minimally invasive surgery. For example, the medical instrument is an instrument with a minimized shaft diameter.

The instrument preferably provides several degrees of freedom for the deflection movement. This comprises for example a variable deflection in several directions (for example downward and from right to left, for example from the point of view of an observer). With coordinated control, the end effector can be deflected in any or almost any desired manner in a plane perpendicular to the longitudinal axis of the shaft, at least in exemplary embodiments. This is comparable to a clock hand, which can assume any positions (from 0.00 h to 12.00 h) on a dial with a 12-hour division. Moreover, in exemplary embodiments, a variation of the degree of the deflection (or kink angle) is also conceivable. With a deflection of 90°, the end effector is oriented perpendicular to the axis of the shaft.

In exemplary embodiments, a deflection of the end effector is characterized by an angle position (pointer), for example between 0° and 360°, and a degree of the deflection (kink angle), for example between 0° (concentric to the longitudinal axis) and 90° (perpendicular to the longitudinal axis) or even more. Other embodiments are conceivable. In an exemplary embodiment, the deflection can be controlled incrementally or steplessly.

A degree of freedom is, for example, a degree of freedom of movement of the instrument or of its end effector. However, it can also be generally understood as a function, in particular a function that comprises a movement of at least one element of the instrument. For example, the opening and closing of the jaw part can also be interpreted as a degree of freedom of the instrument.

According to an exemplary embodiment, two or more of the drives are oriented parallel to one another, wherein preferably two or more of the drives are arranged parallel to a longitudinal axis of the shaft and distributed about the longitudinal axis. In an exemplary embodiment, four drives are provided which are each arranged about the longitudinal axis, offset by 90° to one another in relation to the longitudinal axis. In an exemplary embodiment, the drives are arranged at the same axial position along the longitudinal axis.

According to an exemplary embodiment, the control trains are designed as control wires, in particular as control wires that can be subjected to tensile loading. The control wires are made of nitinol, for example. It will be appreciated that control trains and control wires can also be subjected at least partially to a shear load, at least in exemplary embodiments. In alternative embodiments, the control trains can also be designed as control rods, in particular as flexible control rods or as sufficiently elastic control rods.

According to a further exemplary embodiment, the end effector is deflectable relative to the shaft, wherein a deflectable portion is provided which comprises at least one ball element with spherical surfaces, which is arranged between a proximal ball guide and a distal ball guide, and wherein the at least two control trains are coupled to the distal ball guide in order to deflect the end effector. In an exemplary embodiment, the deflectable portion is arranged at the transition between the shaft and the end effector.

In an exemplary embodiment, the deflectable portion is constructed similarly to a vertebral column. In other words, two or more ball-shaped elements are arranged in series and are each designed between two guides in the form of sockets/socket discs. In this way, considerable degrees of deflection (kink angles) can be achieved.

According to a further exemplary embodiment, a first and a second control train form a pair which is assigned to one degree of freedom of the instrument. According to a further exemplary embodiment, the control trains of the pair are alternately subjected to tension by an associated drive. The two control trains of a pair are preferably alternately subjected to tension, i.e. alternately pulled in the distal direction, by a single drive. The respective other control train performs an oppositely directed compensating movement and, at least in exemplary embodiments, is slightly pretensioned in order to reduce play.

When a first control train of the pair is subjected to tension and as a result of this is pulled in the proximal direction, the other control train (depending on the design of the deflectable portion) is moved in the opposite direction (compensating movement), i.e. is pulled distally (on account of the deflection of the deflectable portion) and/or pushed distally (on account of the pushing movement of the carrier). By contrast, when a second control train of the pair is subjected to tension and as a result of this is pulled in the proximal direction, the other control train (depending on the design of the deflectable portion) is moved in the opposite direction (compensating movement). This applies at least for exemplary embodiments. In an exemplary embodiment, the drives are designed as push and/or pull drives. In other words, in an exemplary embodiment, a drive can push a carrier in the distal direction and/or pull it in the proximal direction, the movement being transmitted to the control train coupled to the carrier.

In this way, in exemplary embodiments, it is possible to ensure a movement that has no play or minimal play, in particular a deflection that has minimal play or no play. In other words, the end effector can be precisely positioned and oriented for example via a deflection movement. For this purpose, in an exemplary embodiment, the deflectable portion is provided between the shaft and the end effector. In exemplary embodiments, the deflectable portion is assigned to the shaft. In exemplary embodiments, the deflectable portion is assigned to the end effector. This is not to be understood as limiting the disclosure.

In an exemplary embodiment, an even number of control trains is provided, of which in each case two form a pair for controlling a degree of freedom of the instrument. This applies in particular to those control trains which are used for deflecting the end effector. For example, two, four, six or eight control trains are provided, which form one pair, two pairs, three pairs or four pairs.

However, this does not rule out an odd number of control trains being provided in total. In an exemplary embodiment, one control train is designed to open or close jaw parts of the end effector. This can take place for example counter to a restoring force, such that a single control train suffices, for example because restoring is provided by a spring.

According to a further exemplary embodiment, a single drive is assigned to the two control trains of a pair. If a single drive controls two control trains, this reduces the overall number of drives that are needed. Moreover, in this way, a state with minimal play or no play can be achieved if the drive tensions the control trains alternately and the respective other control train is slightly pretensioned. In a configuration with four control trains, there are therefore two drives, and in a configuration with eight control trains, there are four drives, at least in exemplary embodiments. It will be appreciated that additional drives can be provided, for example for opening/closing the jaw part.

According to a further exemplary embodiment, the two control trains of a pair are arranged, at least at the distal end, offset by 180° to each other with respect to the longitudinal axis of the shaft. In other words, the two control trains are arranged on mutually opposite sides of the shaft or of the longitudinal axis of the latter. In this way, a deflection movement and the associated reversal movement can be realized without a restoring spring or the like.

In an exemplary embodiment, the two control trains are arranged offset by 180° to each other with respect to the longitudinal axis at the distal end of the shaft, for example at a distal coupling site or a distal ball guide of the deflectable portion. Accordingly, an alternating pulling movement in the proximal direction can cause a deflection movement from a neutral position and also a reversal movement into the neutral position, by one or the other control train being pulled in the proximal direction. The respectively opposite control train preferably performs a compensating movement.

In an exemplary embodiment, the drive is designed to be self-locking. This entails for example a sufficiently high friction between movable parts of the drive, which parts are coupled to the carriers of the two control trains of the pair. If the static friction is sufficiently high, the end effector remains in its deflected state. The static friction results, for example, from participating coupling elements, for example constituent parts of a threaded spindle drive. Alternatively or in addition, electric motors can be used which provide a correspondingly high static moment. This can also contribute to reducing play.

According to a further exemplary embodiment, the drive can be operated in a first direction of rotation and in a second direction of rotation, wherein in the first direction of rotation the first control train of the pair is pulled proximally and in the second direction of rotation the second control train of the pair is pulled proximally. Thus, a single motor (for example an electric motor) can be used to alternately pull the two control trains in the proximal direction via their carriers. To do this, it is simply necessary to operate the motor with alternating rotation (clockwise, anticlockwise).

According to a further exemplary embodiment, the drive is designed as a thread drive and is provided with a spindle, the latter having two oppositely directed thread portions, wherein a first thread portion interacts with the carrier of the first control train, and wherein a second thread portion interacts with the carrier of the second control train.

In this way, an oppositely directed movement of the two carriers of the two control trains of the pair can be effected using just one drive and just one threaded spindle. In other words, the two carriers are moved towards each other or away from each other depending on the direction of rotation of the threaded spindle and on the pitch of the two oppositely directed thread portions, at least in exemplary embodiments. The oppositely directed thread portions comprise, for example, a right-hand thread and a left-hand thread. In an exemplary embodiment, the pitch of the right-hand thread and of the left-hand thread is identical. In this way, the movement of the two control trains of the pair can be mechanically synchronized, since sums of the pushing movement and of the pulling movement of the carriers are the same, at least in exemplary embodiments.

According to a further exemplary embodiment, several of the drives are designed as thread drives with two oppositely directed thread portions, wherein the drives each have a spindle, and wherein the spindles are preferably distributed in a circular shape about the longitudinal axis. In this way, the overall number of drives can be further reduced. For example, a single drive is provided in each case for the two control wires of one pair, such that a degree of freedom of the instrument can be controlled.

According to an alternative embodiment, the two control trains of a pair are each assigned a dedicated, separate drive, wherein the two drives can be operated in coordination (if appropriate in a synchronized manner), in order to alternately pull one of the two control trains in the proximal direction. In this way too, a deflection movement can be effected using the two control trains of one pair. In other words, in this embodiment the two drives of a pair are synchronized such that the second drive frees the second control train, i.e. permits a pushing movement of the carrier in the distal direction, when the first drive tensions the first control train, offset by 180°, i.e. pulls the carrier in the proximal direction.

According to a further exemplary embodiment, at least one of the carriers has a rotary bearing, the latter having a first ring and a second ring which are rotatable relative to each other, and wherein the first ring is coupled to the control train and the second ring is coupled to the drive. The first ring is designed for example for coupling the control train. The second ring is designed for example for coupling to the drive. For example, the first ring is designed as inner ring and the second ring is designed as outer ring. For example, the outer ring has a radially outwardly protruding jib which has a hole with an inner thread which is coupled to a spindle of the drive. The first ring and the second ring are rotatable relative to each other. In this way, rotational decoupling between the control trains and the drives of the actuation unit can be realized.

According to a further exemplary embodiment, the end effector is rotatable about a longitudinal axis of the shaft, wherein the rotation of the end effector preferably takes place relative to the drives. In an exemplary embodiment, the rotational movement of the end effector takes place without any influence or other kind of feedback on the remaining degrees of freedom of the instrument, in particular on the current state of pivoting of the end effector. In an exemplary embodiment, the end effector can be rotated relative to a housing or relative to the drives of the actuation unit. In an exemplary embodiment, the end effector is rotatable, together with the shaft, relative to a housing of the actuation unit. In an exemplary embodiment, when the end effector rotates, the control trains for the deflection movement are also rotated, preferably with a decoupling of the rotational movement between the control trains and the drives, for example in the carriers.

According to a further exemplary embodiment, a rotary drive is provided for the rotation movement of the end effector, wherein the rotary drive has an output shaft which is provided with a pinion and which drives a wheel coupled to the shaft. In an exemplary embodiment, the rotary drive is arranged inside the housing, flush with the drives of the carriers at the proximal end of the instrument.

According to a further exemplary embodiment, an effector control train is moreover provided for the end effector, wherein the effector control train can be subjected at least to tension or pressure in order to open or close jaw parts of the end effector. For example, the effector control train is designed as a control rod. For example, the effector control train extends concentrically with respect to the longitudinal axis of the shaft. Accordingly, the control trains for the deflection movement are distributed radially about the effector control train, at least in exemplary embodiments.

According to a further exemplary embodiment, several drives are provided, which are arranged at a common longitudinal position along the longitudinal axis. In an exemplary embodiment, this applies to all of the drives for the deflection movement.

In an exemplary embodiment, the motors of the drives are arranged at the same axial position with respect to the longitudinal axis, for example flush with one another, wherein the spindles at least in part have different lengths, in order to couple the motors to the carriers, which are arranged mutually offset along the longitudinal axis. In an exemplary embodiment, the motors of the drives are each arranged concentrically to the respective spindle.

According to a further exemplary embodiment, the carriers are arranged offset relative to one another along the longitudinal axis, wherein the carriers preferably have jibs oriented offset relative to one another about the longitudinal axis and having thread portions. In other words, the carriers are offset relative to one another in the longitudinal direction and in terms of angles about the longitudinal axis. In this way, a generally compact structure is obtained with low installation space requirements even in the region of the actuation unit. In an exemplary embodiment, the drives are distributed like a revolver magazine about the longitudinal axis.

According to a further exemplary embodiment, at least the relative orientation or the relative position of the jibs of the carriers is constant when the end effector rotates about the longitudinal axis. This is permitted, for example, by rotational decoupling between the control trains and the jib coupled to the spindle.

According to a further exemplary embodiment, the medical instrument comprises eight control trains, which form four pairs, wherein each pair has two control trains offset by 180° relative to each other with respect to a longitudinal axis of the shaft at least at the distal end, wherein each of the eight control trains is coupled to a carrier, and wherein the two carriers of a pair of the control trains are coupled to a common drive. For example, the control trains are offset at 45° to each other in a circular shape about the longitudinal axis.

In a further exemplary embodiment, a control device is moreover provided which permits coordinated, synchronized control of the four drives, in order to control the eight control trains for the desired deflection of the end effector. In this way, fine gradations of the deflection movement can be obtained, in particular as regards the direction and the degree of the deflection.

In a further exemplary embodiment, the medical instrument comprises four control trains, which form two pairs, wherein each pair has two control trains offset by 180° relative to each other with respect to a longitudinal axis of the shaft at least at the distal end, wherein each of the four control trains is coupled to a carrier, and wherein the two carriers of a pair of the control trains are coupled to a common drive. A desired deflection can be achieved in this way. For example, the control trains are each offset at 90° to each other in a circular shape about the longitudinal axis.

With coordinated, synchronized control of the drives, many kinds of movements can be generated reproducibly. In other words, it is possible to effect not only targeted deflections in predetermined directions (for example right-left-up-down from the point of view of a user at the proximal end of the instrument), but also intermediate stages (for example top right, bottom left and the like). In other words, superposed movements of the control trains of different pairs are conceivable, in order to precisely predefine the desired direction and the degree of the deflection.

According to a further aspect, the present disclosure relates to an actuation unit for a medical instrument, in particular a medical instrument with deflectable end effector, with a plurality of drives, at least two control trains for controlling at least one degree of freedom of the instrument, and with at least two carriers, comprising a first carrier and a second carrier, wherein the at least two control trains comprise a first control train and a second control train, and wherein the first control train is coupled to the first carrier and the second control train is coupled to the second carrier, on which a preferably common drive acts in each case in order to generate a pushing movement or pulling movement of the carrier.

The object is achieved in this way too.

In an exemplary embodiment, the two control trains work together to control a degree of freedom of the instrument, for example to deflect the end effector in a defined direction (for example up-down or right-left). In an exemplary embodiment, the common drive is designed in such a way that a (single) drive movement leads to an oppositely directed movement of the first carrier and of the second carrier. In this way, the two control trains can be operated jointly and in opposite directions.

It will be appreciated that the actuation unit can be further developed according to at least one of the herein described embodiments of the medical instrument, and vice versa.

It will be appreciated that the aforementioned features and the features still to be explained below can be used not only in the respectively cited combination but also in other combinations or singly, without departing from the scope of the present disclosure.

BRIEF DESCRIPTION OF THE DRAWINGS

Further features and advantages of the invention will become clear from the following description and explanation of a number of exemplary embodiments and by reference to the drawings, in which.

DETAILED DESCRIPTION

Figure 1:
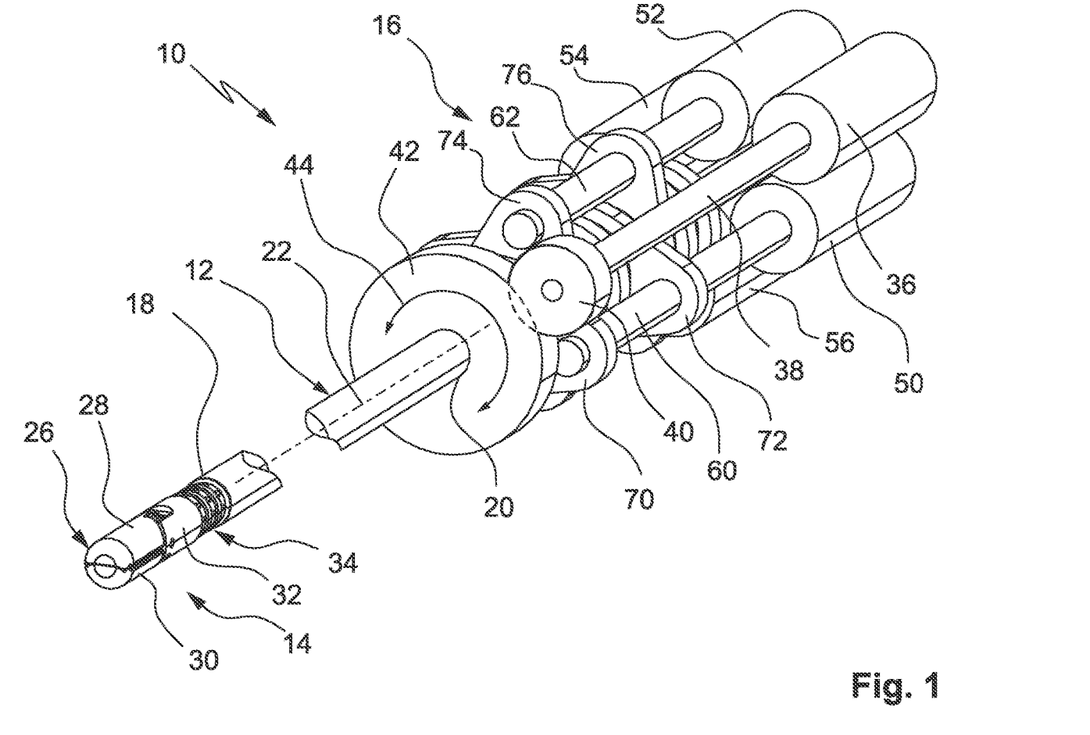
FIG. 1: shows a perspective broken view of a medical instrument, with omission of the housing, seen from the distal end.
Figure 2:
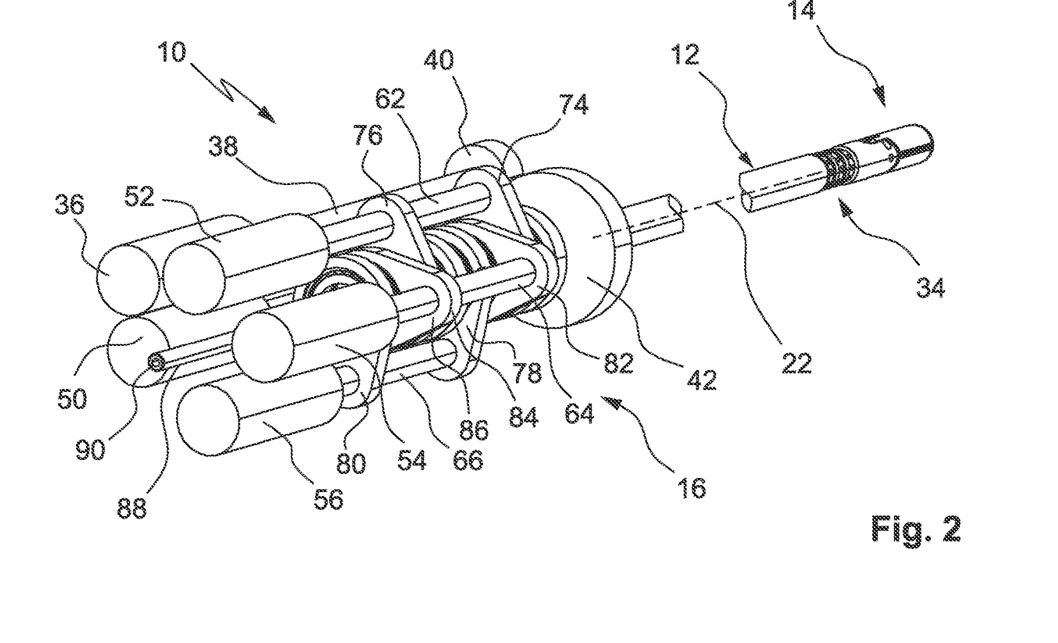
FIG. 2: shows a further perspective broken view of the instrument according to FIG. 1, seen from the proximal end.

FIG. 1 and FIG. 2 are perspective views illustrating an exemplary embodiment of a medical instrument designated overall by reference sign 10. The instrument 10 comprises a shaft 12 which, in the exemplary embodiment, carries an end effector 14. Moreover, an actuation unit 16 is provided for actuating and controlling degrees of freedom of the instrument 10. The shaft 12 extends between a distal end 18 and a proximal end 20. In the exemplary embodiment, the shaft 12 is designed as a hollow shaft and is provided with a rigid shaft body.

The end effector 14 is arranged at the distal end of the instrument 10, i.e. distally with respect to the distal end 18 of the shaft 12. In the exemplary embodiment, the actuation unit 16 is arranged at the proximal end of the instrument 10, i.e. proximally with respect to the proximal end 20 of the shaft 12. The shaft 12 defines a longitudinal axis 22. In the exemplary embodiment, the end effector 14 is a jaw head 26 with two jaw parts 28, 30, which can have an opened and a closed configuration (cf. also FIG. 3 and FIG. 4). The jaw parts 28, 30 are mounted on a support 32.

Between the shaft 12 and the end effector 14 in the exemplary embodiment, a deflectable portion 34 is formed which opens into the support 32. In this way, the end effector 14 can be deflected relative to the shaft 12 or the longitudinal axis 22 (cf. FIG. 5 and FIG. 6). Preferably, the deflectable portion 34 is deflectable not just in one direction (for example up and down or right to left) but in various directions starting from an extended position (concentric to the longitudinal axis 22).

In the exemplary embodiment, the actuation unit 16 comprises a rotary drive 36, which supports a pinion 40 arranged on a shaft 38. The pinion 40 is in engagement with a wheel 42, which is connected to the shaft 12. The wheel 42 is arranged concentric to the shaft 12 and to the longitudinal axis 22 of the latter. The rotary drive 36 and the shaft 38 are arranged parallel to and spaced apart from the longitudinal axis 22. The rotary drive 36 causes a rotation of the shaft 12 and of the end effector 14 about the longitudinal axis 22 of the shaft 12. However, exemplary embodiments without a rotary drive are also conceivable.

The actuation unit 16 moreover comprises a plurality of drives 50, 52, 54, 56 for controlling the deflectable portion 34 for deflection of the end effector 14 (cf. also the rear perspective view according to FIG. 2 in addition to the front perspective view according to FIG. 1). In the exemplary embodiment, a total of four drives 50, 52, 54, 56 are installed for the deflection movement. Each of the drives 50, 52, 54, 56 has a spindle 60, 62, 64, 66. In the exemplary embodiment, the drives 50, 52, 54, 56 and the respectively associated spindles 60, 62, 64, 66 are distributed in a circular shape about the longitudinal axis 22, for example at a respective angular offset of 90°.

The spindle 60 coupled to the drive 50 is coupled to two carriers 70, 72, which are axially offset relative to each other. The spindle 62 coupled to the drive 52 is coupled to two carriers 74, 76, which are axially offset relative to each other. The spindle 64 coupled to the drive 54 is coupled to two carriers 78, 80, which are axially offset relative to each other. The spindle 66 coupled to the drive 56 is coupled to two carriers 82, 84, which are axially offset relative to each other. The carriers 70, 72, 74, 76, 78, 80, 82, 84 are staggered, axially offset relative to each other, and in part rotationally offset relative to each other along the longitudinal axis 20.

In the exemplary embodiment according to FIGS. 1 and 2, the drives 50, 52, 54, 56 are arranged flush with one another in relation to the longitudinal axis 22, i.e. at the same axial position. The length of the spindles 60, 62, 64, 66 is in each case adapted to the position and spacing of the associated carriers 70, 72, 74, 76, 78, 80, 82, 84. In FIG. 2, a jib of the carrier 84 is indicated by reference sign 86 (see also FIG. 11 in this connection).

In the exemplary embodiment, the two carriers 70, 72, 74, 76, 78, 80, 82, 84 assigned respectively to one of the drives 50, 52, 54, 56 are arranged congruently in a front view. In other words, the respective jib 86 of the two respective carriers 70, 72, 74, 76, 78, 80, 82, 84 of such a pair is arranged in an identical rotary angle position with respect to the longitudinal axis 22.

Figure 3:
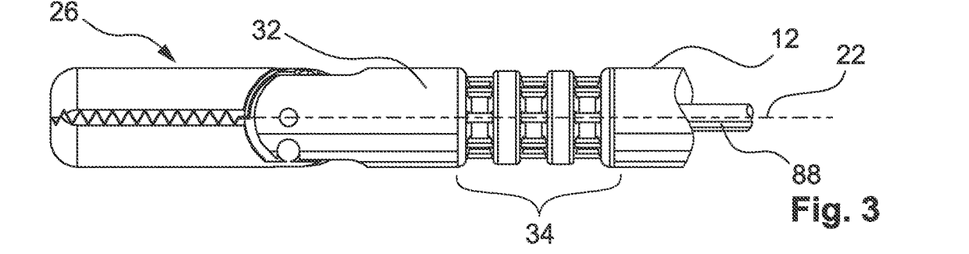
FIG. 3: shows a detail view of a distal end of a medical instrument having an end effector, with closed jaw head.
Figure 4:
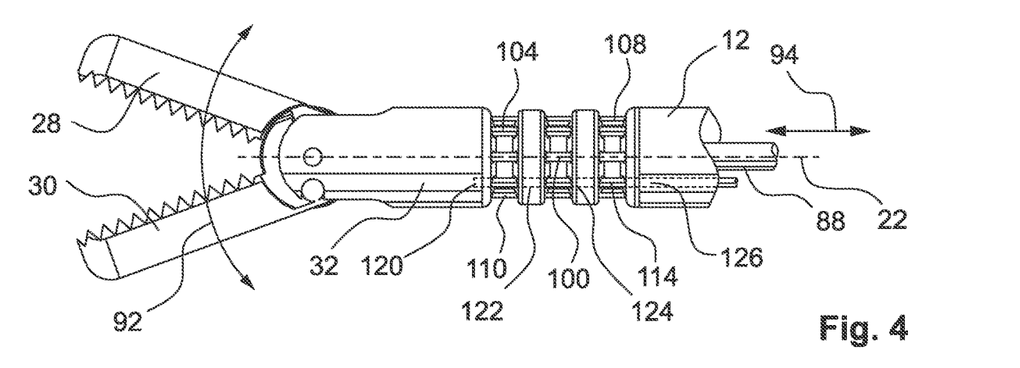
FIG. 4: shows a further view based on the view according to FIG. 3, with opened jaw head.

FIG. 3 and FIG. 4 illustrate an example of a degree of freedom of the instrument 10. In the exemplary embodiment, the end effector 14 is designed as a jaw head 26 with two jaw parts 28, 30, which can assume a closed position (FIG. 3) and an opened position (FIG. 4). For this functionality, a control train 88 is provided which is designed as a rod 90 for example (see also FIG. 2 in this connection). In the exemplary embodiment, the control train 88 is arranged concentrically to the longitudinal axis 22 at least in part inside the shaft 12. The control train 88 extends through the shaft 12 and, at the distal end of the instrument 12, is coupled to the jaw head 26 (not shown in detail in FIGS. 3 and 4). Depending on the type of control chosen, the jaw head 26 can be opened or closed by a pulling movement or pushing movement of the control train 88 (see also the double arrow 94 in FIG. 4). Such a movement can be controlled manually or by motor. In FIG. 4, a curved double arrow 92 illustrates the actuation of the jaw parts 28, 30.

Figure 12:
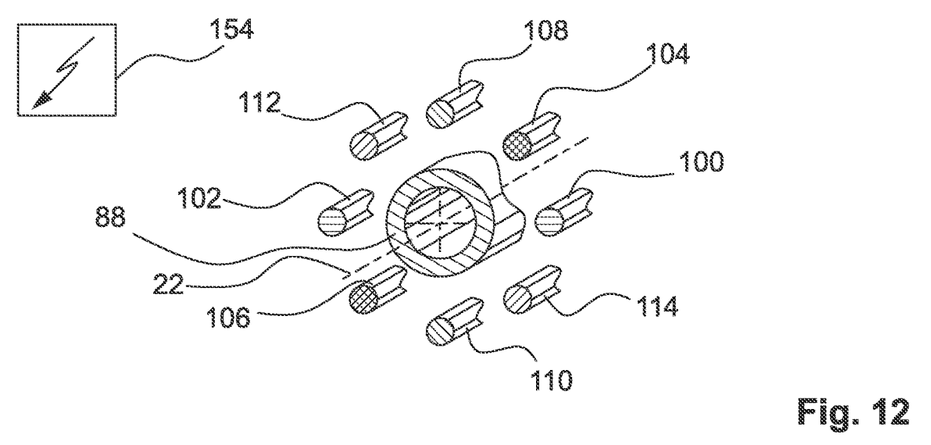
FIG. 12: shows a schematic, simplified perspective view of a plurality of control trains, which are distributed in a circular shape about a longitudinal axis.

It can also be seen from FIGS. 3 and 4 that so-called control trains 100, 102, 104, 106, 108, 110, 112, 114 are installed which extend axially through the shaft 12 of the instrument 10 to the end effector 14 or to the support 32 of the latter (see also the schematic overview according to FIG. 12). In other words, the control trains 100, 102, 104, 106, 108, 110, 112, 114 extend through the deflectable portion 34. The control trains 100, 102, 104, 106, 108, 110, 112, 114 serve for the initiation and control of the deflection movement of the end effector 14, hence the manipulation of the deflectable portion 34 (see also FIG. 5 and FIG. 6 in this connection).

In FIG. 4, reference sign 120 indicates a distal coupling for the control train 114. Moreover, further (concealed) guides 122, 124 and 126 for the control train 114 are indicated. Similar guides are provided for the remaining control trains 100, 102, 104, 106, 108, 110, 112. The respective distal coupling 120 ensures that pulling movements on the control trains 100, 102, 104, 106, 108, 110, 112, 114 are transmitted to the support 32 for deflection of the latter. The control trains 100, 102, 104, 106, 108, 110, 112, 114 are routed in an at least partially concealed manner through the instrument 10 and protrude through the shaft 12 between the distal end 18 and the proximal end 20. At their proximal end, the control trains 100, 102, 104, 106, 108, 110, 112, 114 are coupled to the carriers 70, 72, 74, 76, 78, 80, 82, 84, in each case one control train to one of the carriers. In this way, the control trains 100, 102, 104, 106, 108, 110, 112, 114 can be pulled proximally and if necessary pushed distally, or relaxed, via the drives 50, 52, 54, 56 and the spindles 60, 62, 64, 66 of the latter.

Figures 5, 6:
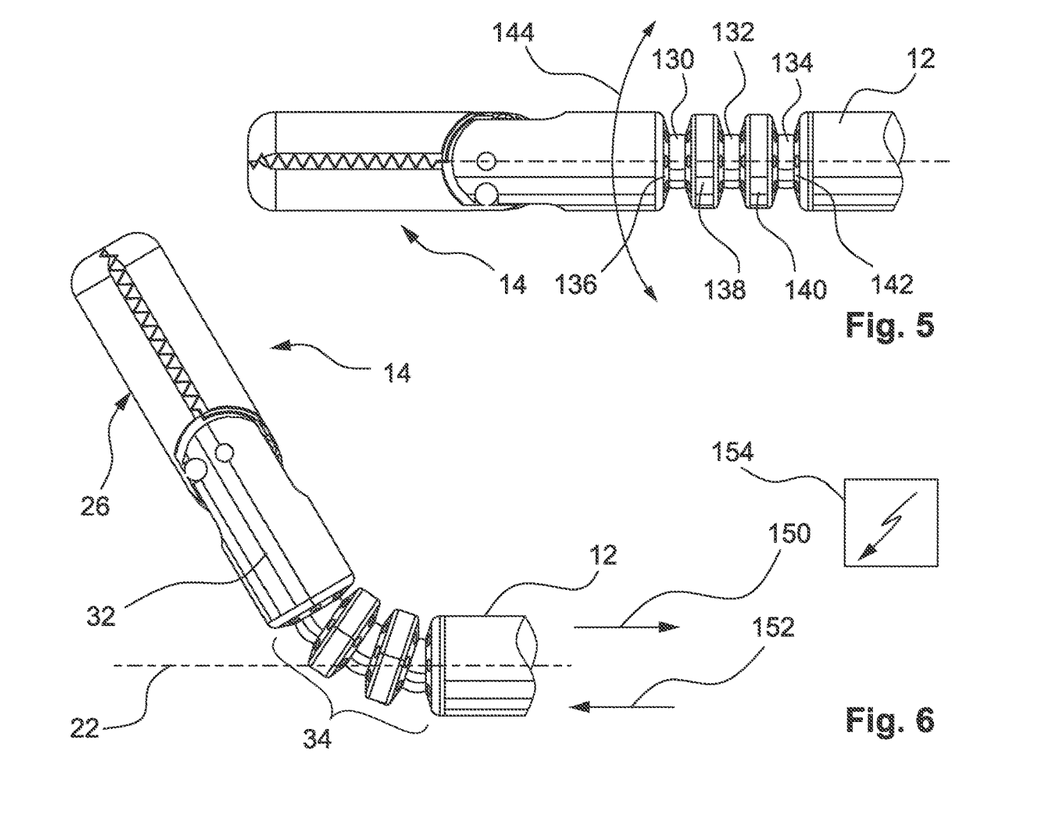
FIG. 5: shows a detail view of a distal end of a medical instrument with end effector in a non-deflected position.
FIG. 6: shows a further view based on the view according to FIG. 5, in a deflected position.

For the sake of clarity, the control trains 100, 102, 104, 106, 108, 110, 112, 114 have not been shown in FIGS. 5 and 6. FIG. 5 shows a non-deflected state of the end effector 14. FIG. 6 shows an at least partially deflected state of the end effector 14 through corresponding deformation of the deflectable portion 34. The exemplary embodiment is configured such that the end effector 14 is also deflectable in other directions relative to the longitudinal axis 22, for example perpendicularly to the viewing plane.

The deflectable portion 34 has ball elements 130, 132, 134, which are each arranged between two ball guides 136, 138, 140, 142. The ball guides 136, 138, 140, 142 can also be designated as ball sockets. The ball guides 138, 140 can also be designated as guide discs. The ball guide 136 is a distal ball guide to which the control trains 100, 102, 104, 106, 108, 110, 112, 114 are coupled in order to act, via the distal coupling 120 (FIG. 4) on the support 32 of the end effector 14, so as to deflect the end effector 14. A pivoting movement, as an example of the deflection, is shown in FIG. 5 by a curved double arrow with reference sign 144.

The deflection indicated in FIG. 6 is brought about when some of the control trains 100, 102, 104, 106, 108, 110, 112, 114, in particular the mutually opposite control trains 108 and 110 (FIG. 8 and FIG. 12), are controlled so as to deform the deflectable portion 34 in the desired manner. In FIG. 6, an arrow 150 illustrates a pulling movement, whereas an arrow 152 illustrates a compensating movement in the opposite direction (distally directed movement). As a result of these movements, one side of the deflectable portion 34 is compressed and the other side expanded. This can be brought about by the control train 108 being pulled proximally, and if necessary the opposite control train 110 being relaxed or even pulled/pushed distally. In the exemplary embodiment, the compensating movement is also brought about by the tilting of the distal ball guide 136 (and if appropriate of further ball guides 138, 140) to which the control trains 100, 102, 104, 106, 108, 110, 112, 114 are coupled (distal coupling 120). Here, the tilting in reaction to the proximally directed pulling movement of one of the control trains 100, 102, 104, 106, 108, 110, 112, 114 ensures a distally directed pulling movement of the opposite control train 100, 102, 104, 106, 108, 110, 112, 114 offset by 180°.

The deflection of the end effector 14, as shown in FIG. 6, requires a targeted manipulation of several of the control trains 100, 102, 104, 106, 108, 110, 112, 114. This can lead to a reduction in the movement clearance or reversal clearance. Figuratively speaking, in the given configuration in FIG. 6, the control trains 104, 108, 112 above the longitudinal axis 22 are to be at least partially subjected to tension, i.e. pulled proximally, whereas the control trains 106, 110, 114 below the longitudinal axis are to be relaxed or moved distally "in mirror inversion". In these circumstances, the control trains 100, 102 lie in the "neutral axis" (zero line) (see also FIG. 12). This is not to be understood as limiting the disclosure.

A simultaneous control of the drives 50, 52, 54, 56 is equally advantageous for manipulating the control trains 100, 102, 104, 106, 108, 110, 112, 114 and the whole deflectable portion in the desired manner. For this purpose, a control unit is indicated by reference sign 154 in FIG. 6. Two control trains 100, 102, 104, 106, 108, 110, 112, 114 offset by 180° form a pair which, in the exemplary embodiment, is coupled to a single drive 50, 52, 54, 56.

Figure 7:
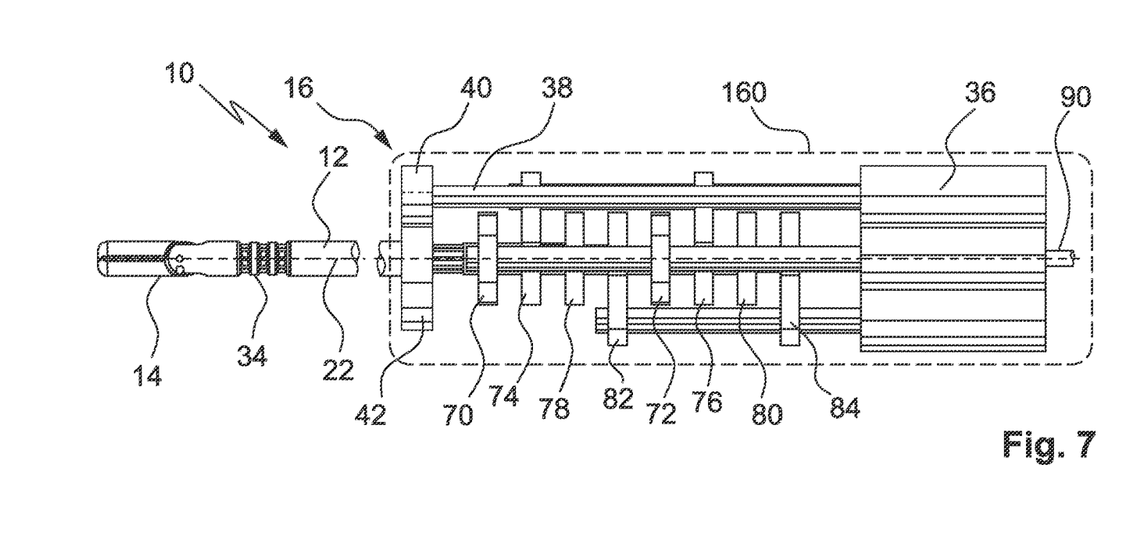
FIG. 7: shows a broken and simplified side view of a medical instrument with deflectable portion and actuation unit.
Figure 8:
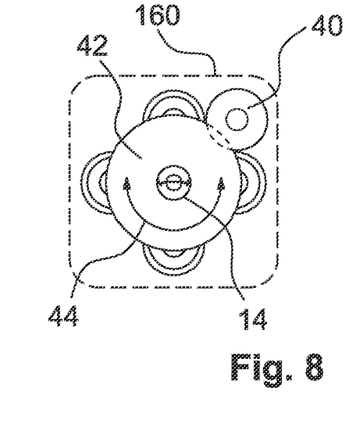
FIG. 8: shows a front view of the instrument according to FIG. 7.
Figure 9:
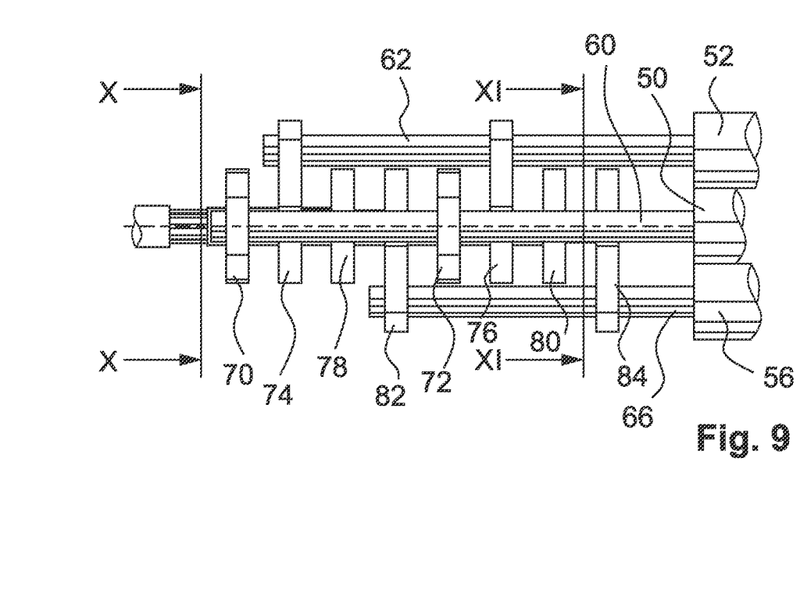
FIG. 9: shows an enlarged partial side view of the instrument according to FIG. 7, for illustrating the actuation unit.
Figure 10:
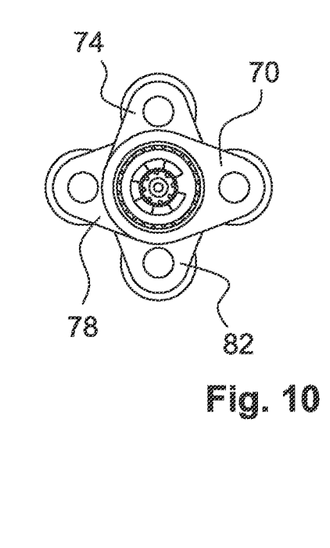
FIG. 10: shows a sectional view of the instrument according to FIG. 9 based on the line X-X in FIG. 9, for illustrating the actuation unit.
Figure 11:
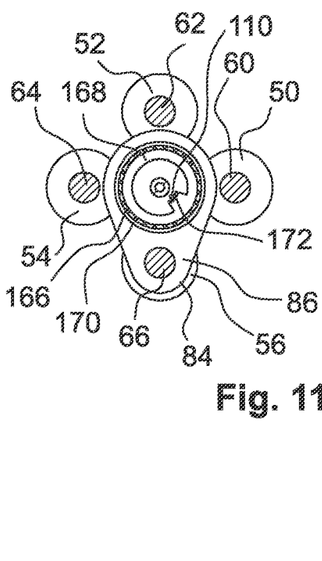
FIG. 11: shows a further sectional view of the instrument according to FIG. 9 based on the line XI-XI in FIG. 9, for illustrating the actuation unit.

With additional reference to FIGS. 7 and 8 and also to FIGS. 9-11 based thereon, the control of individual control trains (or pairs of control trains 100, 102, 104, 106, 108, 110, 112, 114) with just a single drive 50, 52, 54, 56 is explained in more detail.

FIG. 7 shows a broken side view of the instrument 10, with a dashed line symbolizing a housing 160 for the actuation unit 16. FIG. 8 shows a corresponding front view. FIG. 9 shows an enlarged partial side view based on FIG. 7, with omission of various elements. FIGS. 10 and 11 show sectional views along lines X-X and XI-XI in FIG. 9. The optional rotary drive 36 and the housing 160 have been omitted from the views in FIGS. 9-11. In addition to FIGS. 7-11, FIG. 12 shows an enlarged schematic view of the control trains 100, 102, 104, 106, 108, 110, 112, 114. Moreover, FIG. 13 in addition shows an enlarged lateral sectional view of selected components from the view according to FIG. 9.

The actuation unit 16 adjoining the shaft 12 is of compact construction, with the drives 50, 52, 54, 56 being distributed in a circular shape about the longitudinal axis 22. The drives 50, 52, 54, 56 and their spindles 60, 62, 64, 66 are in each case arranged offset by 90° to each other about the longitudinal axis 22 and parallel to the latter (see FIG. 11). FIG. 8 illustrates that, in the exemplary embodiment, a gap between two drives 50, 52 has been used for the placement of the rotary drive 36 and the shaft 38. This is not to be understood as limiting the disclosure. The drives 50, 52, 54, 56 are, for example, regulated electromotive drives with a drive shaft which, in the exemplary embodiment, forms the respective spindle 60, 62, 64, 66.

In the exemplary embodiment, the carriers 70, 72, 74, 76, 78, 80, 82, 84 are arranged with a constant axial spacing along the longitudinal axis 22 between the drives 50, 52, 54, 56 and the shaft 12. If the exemplary embodiment provides a rotary drive 36 for the shaft 12 and the end effector 14, a corresponding wheel 42 is coupled thereto at the proximal end 20 of the shaft 12. The wheel 42 is driven via a pinion 40 which sits on the shaft 38 of the rotary drive 36 (see also FIG. 8 with the double arrow 44 for illustrating the rotation movement).

The components of the rotary drive 36 and the housing 160 have been omitted from the views in FIGS. 9-11. The carriers 70, 72, 74, 76, 78, 80, 82, 84 form four pairs, which are in each case coupled to one of the spindles 60, 62, 64, 66 of the drives 50, 52, 54, 56. In the exemplary embodiment, the carriers 70, 72, 74, 76, 78, 80, 82, 84 of a pair are in each case at a constant axial spacing from each other.

FIGS. 10 and 11 illustrate that each of the carriers 70, 72, 74, 76, 78, 80, 82, 84 has a radially outwardly protruding jib 86, through which the associated spindle 60, 62, 64, 66 passes.

In addition, FIG. 11 shows that the carriers (shown here: carrier 84) each have a rotary bearing 166 for rotational decoupling between the spindle (shown here: spindle 66) and the associated control train (here: control train 110). Such a functionality is conceivable at least in some exemplary embodiments in order to permit a relative rotation of the end effector 14 relative to the actuation unit 16 without effects on the actual deflection status (direction and/or degree of the deflection) of the end effector 14. The rotary bearing 166 is shown in lateral section, likewise in the schematic view according to FIG. 13.

Figure 13:
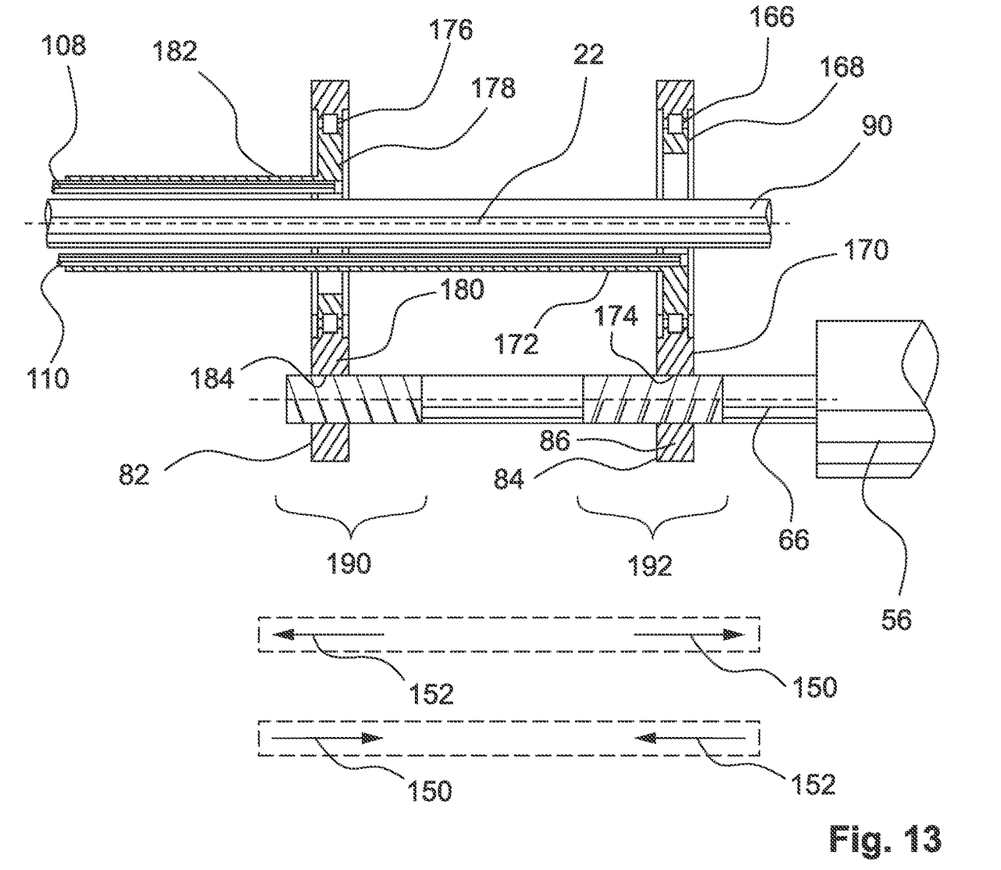
FIG. 13: shows an enlarged lateral and sectioned partial view based on the view according to FIG. 9, with various elements concealed for the sake of clarity.

The rotary bearing 166 comprises a first ring 168, designed as inner ring, and a second ring 170, designed as outer ring. The first ring 168 and the second ring 170 are rotatable relative to each other. On the first ring 168, an extension piece 172 is formed to which the control train 110 is coupled (see again FIG. 13). The jib 86, which provides a guide for the spindle 66, is formed on the second ring 170. In this connection, FIG. 13 illustrates that the jib 86 provides an inner thread 174 for the spindle 66. The design of the carrier 84 illustrated in FIGS. 11 and 13 is representative for all of the carriers 70, 72, 74, 76, 78, 80, 82, 84.

FIG. 12 is a schematic perspective view illustrating the circular arrangement of the control trains 100, 102, 104, 106, 108, 110, 112, 114 about a common centre which, in the exemplary embodiment, is defined by the longitudinal axis 22. The angular offset here is in each case 45°. The control train 88, designed as a rod for example, for opening and closing the jaw head 26 is arranged concentrically with respect to the longitudinal axis 22. Based on the hatching of the control trains 100, 102, 104, 106, 108, 110, 112, 114, FIG. 2 illustrates the respective association for forming a pair. The control trains 100, 102 form a first pair. The control trains 104, 106 form a second pair. The control trains 108, 110 form a third pair. The control trains 112, 114 form a fourth pair. By specifically coordinated and synchronized control of the control trains 100, 102, 104, 106, 108, 110, 112, 114, deflections of the end effector 14 can be brought about in diverse and, optionally, any desired directions relative to the longitudinal axis 22. For this purpose, the control unit 154 (only symbolically indicated) is provided, which in particular controls the drives 50, 52, 54, 56 in a suitable manner.

It will be appreciated that, in a departure from the embodiment shown in FIG. 12 with a total of four pairs, embodiments with two pairs, three pairs or optionally just one pair of control trains 100, 102, 104, 106, 108, 110, 112, 114 are also conceivable. In principle, more than four pairs are also conceivable. The aforementioned U.S. Pat. No. 5,454,827 A illustrates an embodiment of a deflection mechanism with two pairs of control wires, to which reference is hereby made.

FIG. 13 illustrates the functionality of the motor drive 56 as representative of the plurality of drives 50, 52, 54, 56. The spindle of the drive 56 is coupled to the carrier 82 and the carrier 84. The carrier 82 is coupled to the control train 108. The carrier 84 is coupled to the control train 110. In the manner already described above, the carrier 84 is provided with a rotary bearing 166. The spindle 66 passes through the carrier 84 in the region of the jib 86 thereof, in which an opening with inner thread 174 is formed. The control train 110 is coupled to an extension piece 172 of the carrier 84.

The carrier 82 equally comprises a rotary bearing 176, which is formed between a first ring 178 and a second ring

180. The first ring 178 serves as inner ring and has an extension piece 182, to which the control train 108 is coupled. The second ring 180 serves as outer ring and, in the region of its jib, is provided with an opening with inner thread 184, through which the spindle 66 passes. The spindle 66 is a threaded spindle.

The spindle 66 has a first thread portion 190 and a second thread portion 192. The thread portion 190 is assigned to the carrier 82. The thread portion 192 is assigned to the carrier 84. The two thread portions 190, 192 have opposite pitches, and the inner threads 174, 184 of the carriers 82, 84 are adapted thereto. This has the effect that, when a rotational movement of the spindle 66 is induced by the drive 56, one of the two carriers 82, 84 is moved proximally and the other is moved distally. An opposite rotational movement of the spindle 66 leads to an opposite movement of the two carriers 82, 84. In other words, the two carriers 82, 84 are moved toward or away from each other depending on the driving direction of the spindle 66 (in this connection see the respective arrows 150, 152 in FIG. 13).

In other words, one of the two control trains 108, 110 is pulled proximally, whereas the other of the two control trains 108, 110 is relaxed or even pushed distally. In this way overall, the deflection of the end effector 14 as illustrated in FIGS. 5 and 6 can be achieved.

By virtue of the opposite thread portions 190, 192 in the exemplary embodiment, it is ensured that the two control trains 100, 102, 104, 106, 108, 110, 112, 114 of a pair are moved by the same amount with different movement directions. This can also contribute to minimizing play. Moreover, the number of drives that are needed can be reduced in this way.

The control unit 154 (FIG. 12) synchronizes the drives 50, 52, 54, 56, with some of the control trains 100, 102, 104, 106, 108, 110, 112, 114 having to be moved more than the others, depending on the desired direction of the deflection with respect to the longitudinal axis 22.

In an exemplary embodiment, the drive 56 (representative of each of the drives 50, 52, 54, 56) is designed to be self-locking. This can be achieved, for example, through the design of the thread portions 190, 192. In the context of the present disclosure, the term self-locking is to be understood as a design in which a respective deflection state of the end effector 14 is safely maintained after the desired position has been reached. In exemplary embodiments, this also applies when the drives 50, 52, 54, 56 do not have current passing through them. Self-locking has the effect, for example, that a manipulation directly at the distal end of the instrument 12, for example a manual "movement" of the end effector 14 or "bending" of the deflectable portion 34, is made difficult or is suppressed.

Figure 14:
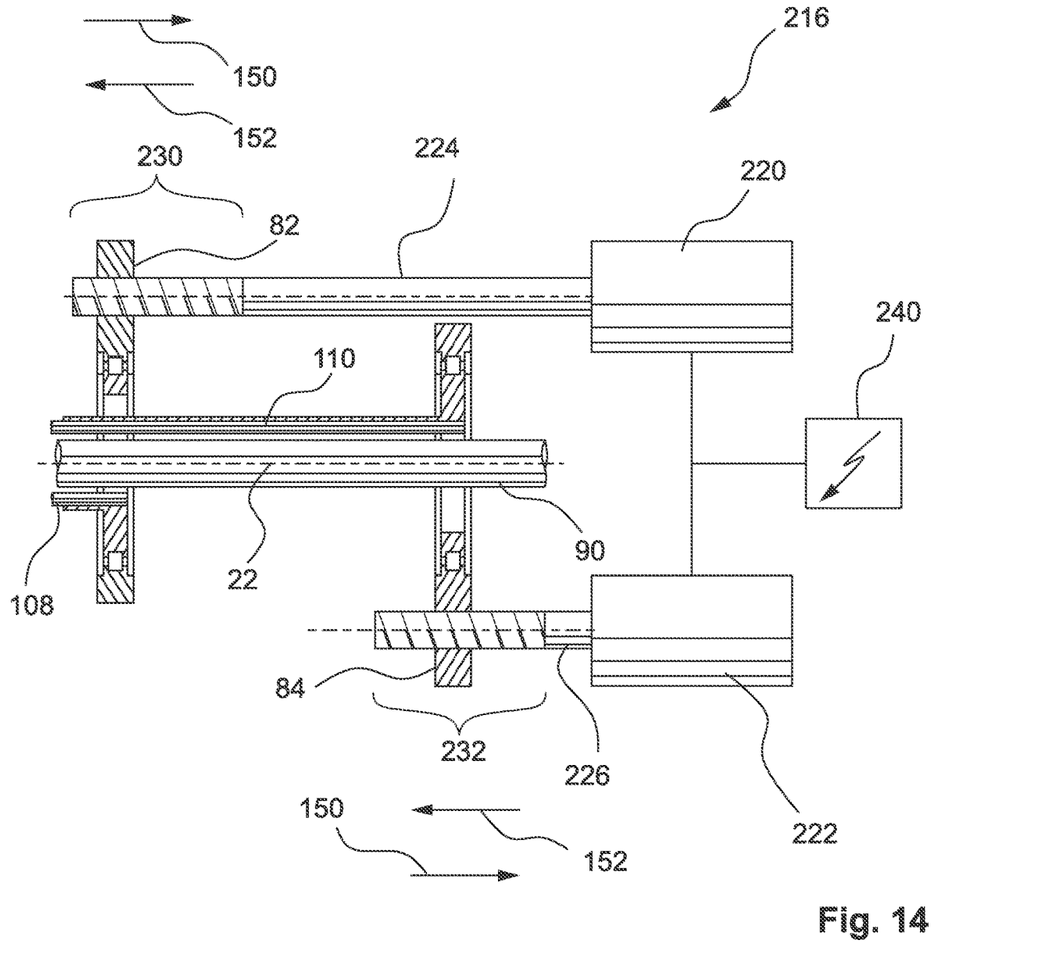
FIG. 14: shows a further lateral and sectioned partial view illustrating an alternative embodiment of a control unit of a medical instrument.

FIG. 14 illustrates an alternative embodiment of an actuation unit designated overall by reference sign 216. It is mainly the aspects of the design that deviate from the embodiments according to FIGS. 1-13 that are described below. One difference from the design illustrated in FIG. 13 is that the two control trains 108, 110 of a pair, which are mutually offset by approximately 180° in relation to the longitudinal axis, are controlled by two motors 220, 222. A first drive 220 is coupled to the control train 108 via a spindle 224 and the carrier 82. A second drive 222 is coupled to the control train 110 via a spindle 226 and the carrier 84. The carrier 82 is offset distally with respect to the carrier 84.

Each of the two control trains 108, 110 is controlled by a dedicated, separate drive 220, 222, in particular in the form of an electric motor with drive spindle. The spindle 224 has a thread portion 230. The spindle 226 has a thread portion 232. The carriers 82, 84 are accordingly provided with a corresponding inner thread. Depending on the chosen direction of rotation of the drives 220, 222, the carriers 82, 84 can be pulled proximally (see the arrows 150) or pushed distally (see the arrows 152). The two control trains 108, 110 form a common pair and can therefore be alternately subjected to tension in order to deflect the end effector 14 (see FIGS. 5 and 6).

FIG. 13 shows a design in which mechanical synchronizing is provided on account of the opposite thread portions 190, 192. In FIG. 14, reference sign 42 indicates a control unit which controls the two drives 220, 222 in a targeted and synchronous manner, such that the desired opposite movements of the carriers 82, 84 are achieved. This allows the end effector 14 to be deflected with no or minimal play. It will be appreciated that, besides the two control trains 108, 110, the others of the control trains 100, 102, 104, 106, 108, 110, 112, 114 can also each be controlled with a separate drive. Accordingly, in the exemplary embodiment with a total of eight control trains 100, 102, 104, 106, 108, 110, 112, 114, eight drives and eight threaded spindles are provided. The two drives assigned to a respective pair of the control trains 100, 102, 104, 106, 108, 110, 112, 114, offset by 180°, are controlled in a synchronized manner such that the mutually opposite control trains 100, 102, 104, 106, 108, 110, 112, 114 can be pulled in the proximal direction or released or pushed in the distal direction.

Figure 15:
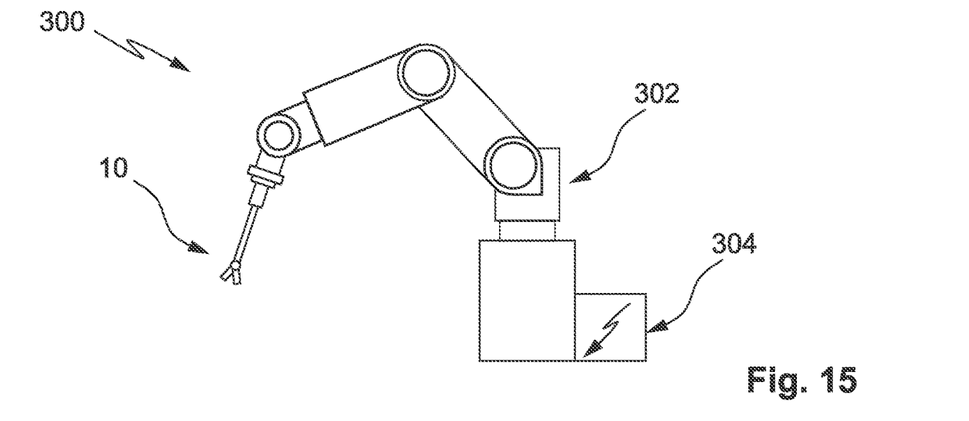
FIG. 15: shows a simplified view of a manipulator for manipulating a medical instrument.

FIG. 15 is a schematic view illustrating an exemplary embodiment of a medical system 300 which serves for handling and guiding an instrument 10 according to the disclosure. The system 300 comprises a manipulation device 302 for holding and guiding the instrument 10. The manipulation device 302 can also be designated as a manipulator. For example, the manipulation device 302 is a surgical robot. The system 300 moreover comprises a control device 304, which controls degrees of freedom of the manipulation device 302. Moreover, the control device 304 can also be designed to control the degrees of freedom of the instrument 10 within the meaning of the present disclosure.

The disclosure relates to an actuation unit 16 for a medical instrument 10 and to a medical instrument 10 with a shaft 12 which extends between a proximal end 20 and a distal end 22, wherein the instrument 10 is designed at the distal end 22 to receive an end effector 14, an actuation unit 16, 216 which is assigned to the proximal end of the shaft 12, and which has a plurality of drives 50, 52, 54, 56, and with at least two control trains 100, 102, 104, 106, 108, 110, 112, 114 which extend through the shaft 12, wherein the at least two control trains 100, 102, 104, 106, 108, 110, 112, 114 can be used for controlling at least one degree of freedom of the instrument, in particular for deflecting the end effector 14, wherein the at least two control trains 100, 102, 104, 106, 108, 110, 112, 114 comprise a first control train 100, 104, 108, 112 and a second control train 102, 106, 110, 114, and wherein the first control train 100, 104, 108, 112 is coupled to a first carrier 70, 74, 78, 82 and the second control train 102, 106, 110, 114 is coupled to a second carrier 72, 76, 80, 84, on which a drive 50, 52, 54, 56 acts for generating a pushing movement or pulling movement of the carrier 70, 72, 74, 76, 78, 80, 82, 84. It will be appreciated that the actuation unit can be developed according to at least one of the herein described embodiments of the medical instrument, and vice versa. It will be appreciated that the aforementioned features and the features still to be explained below can be used not only in the respectively cited combination but also in other combinations or singly, without departing from the scope of the present disclosure.

The invention claimed is:

1. A medical instrument comprising:
a shaft which extends between a proximal end and a distal end, wherein the instrument is configured at the distal end to receive an end effector,
an actuation unit which is assigned to the proximal end of the shaft, and includes a plurality of drives, and at least two control trains which extend through the shaft, wherein the at least two control trains can be used for controlling at least one degree of freedom of the instrument to deflect the end effector, wherein the at least two control trains comprise a first control train and a second control train, and wherein the first control train is coupled to a first carrier and the second control train is coupled to a second carrier, on which a drive acts for generating a pushing movement or pulling movement of the carrier, wherein two control trains of a pair of control trains are assigned a single drive, and wherein the two control trains of the pair of control trains are arranged, at least at the distal end, offset by 180° to each other with respect to the shaft, wherein the drive can be operated in a first direction of rotation and in a second direction of rotation, and wherein in the first direction of rotation the first control train of the pair is pulled proximally and in the second direction of rotation the second control train of the pair is pulled proximally.

2. The medical instrument according to claim 1, wherein two or more of the drives are oriented parallel to one another, and wherein two or more of the drives are arranged parallel to a longitudinal axis of the shaft and distributed about the longitudinal axis.

3. The medical instrument according to claim 1, wherein the end effector is deflectable relative to the shaft, wherein a deflectable portion is provided which comprises at least one ball element with spherical surfaces, which is arranged between a proximal ball guide and a distal ball guide, and wherein the at least two control trains are coupled to the distal ball guide in order to deflect the end effector.

4. The medical instrument according to claim 1, wherein the first and the second control train form the pair which is assigned to one degree of freedom of the instrument, and wherein the control trains of the pair are alternately subjected to tension by an associated drive.

5. The medical instrument according to claim 1, wherein the drive is designed as a thread drive and has a spindle, the latter having two oppositely directed thread portions, wherein a first thread portion interacts with the carrier of the first control train, and wherein a second thread portion interacts with the carrier of the second control train.

6. The medical instrument according to claim 5, wherein several of the drives are designed as thread drives with two oppositely directed thread portions, wherein the drives each have a spindle, and wherein the spindles are distributed in a circular shape about the longitudinal axis.

7. The medical instrument according to claim 4, wherein the two control trains of a pair are each assigned a dedicated drive, and wherein the two drives can be operated in coordination, in order to alternately subject one of the two control trains to tension.

8. A medical instrument comprising:
a shaft which extends between a proximal end and a distal end, wherein the instrument is configured at the distal end to receive an end effector,
an actuation unit which is assigned to the proximal end of the shaft, and includes a plurality of drives, and at least two control trains which extend through the shaft, wherein the at least two control trains can be used for controlling at least one degree of freedom of the instrument to deflect the end effector, wherein the at least two control trains comprise a first control train and a second control train, and wherein the first control train is coupled to a first carrier and the second control train is coupled to a second carrier, on which a drive acts for generating a pushing movement or pulling movement of the carrier, wherein at least one of the carriers has a rotary bearing, the latter having a first ring and a second ring which are rotatable relative to each other, and wherein the first ring is coupled to the control train and the second ring is coupled to the drive.

9. The medical instrument according to claim 1, wherein the end effector is rotatable about a longitudinal axis of the shaft, and wherein the rotation of the end effector takes place relative to the drives.

10. The medical instrument according to claim 9, wherein a rotary drive is provided for the rotation movement of the end effector, and wherein the rotary drive has an output shaft which is provided with a pinion and which drives a wheel coupled to the shaft.

11. The medical instrument according to claim 1, wherein moreover an effector control train is provided for the end effector, and wherein the effector control train can be subjected at least to tension or pressure in order to open or close jaw parts of the end effector.

12. The medical instrument according to claim 1, wherein several drives are provided, which are arranged at a common axial position along the longitudinal axis.

13. The medical instrument according to claim 1, wherein the carriers are arranged offset relative to one another along the longitudinal axis, and wherein the carriers have jibs offset relative to one another about the longitudinal axis and having thread portions.

14. The medical instrument according to claim 13, wherein at least the relative orientation of the jibs of the carriers to one another is constant when the end effector rotates about the longitudinal axis, or the relative position of the jibs of the carriers to one another is constant when the end effector rotates about the longitudinal axis.

15. The medical instrument according to claim 1, comprising eight control trains, which form four pairs, wherein each pair has two control trains offset by 180° relative to each other with respect to a longitudinal axis of the shaft at least at the distal end, wherein each of the eight control trains is coupled to a carrier, and wherein the two carriers of a pair of the control trains are coupled to a common drive.

* * * * *